United States Patent [19]
Wilson et al.

[11] Patent Number: 5,697,783
[45] Date of Patent: Dec. 16, 1997

[54] ORTHODONTIC BAND

[75] Inventors: Mark J. Wilson, 24515 Chamalea St., Mission Viejo, Calif. 92691; Frank J. Burrell, Jr., Torrance; Farel A. Rosenberg, Beverly Hills, both of Calif.

[73] Assignee: Mark J. Wilson, Misson Viejo, Calif.

[21] Appl. No.: 477,221

[22] Filed: Jun. 7, 1995

Related U.S. Application Data

[63] Continuation-in-part of Ser. No. 326,065, Oct. 18, 1994, abandoned, which is a continuation of Ser. No. 131,309, Oct. 4, 1993, abandoned.

[51] Int. Cl.⁶ ............................................. A61C 7/00
[52] U.S. Cl. ............................................................. 433/23
[58] Field of Search ..................................... 433/23, 39

[56] References Cited

U.S. PATENT DOCUMENTS

| | | | |
|---|---|---|---|
| 632,905 | 9/1899 | Knapp. | |
| 1,304,881 | 3/1919 | Johnson. | |
| 2,007,517 | 2/1935 | Boyd et al. | |
| 3,055,110 | 9/1962 | Kesling | 433/17 |
| 3,138,872 | 6/1964 | Lazarus. | |
| 3,343,247 | 9/1967 | Dillberg et al. | 29/160.6 |
| 3,452,436 | 7/1969 | De Woskin | 433/23 |
| 3,513,545 | 5/1970 | Miller | 433/23 |
| 4,167,813 | 9/1979 | Forster. | |
| 4,192,068 | 3/1980 | Wolfson | 433/23 |
| 4,553,937 | 11/1985 | Ropers | 433/39 |
| 4,840,562 | 6/1989 | Wilson et al. | 433/23 |
| 5,382,160 | 1/1995 | Shemet | 433/39 |

FOREIGN PATENT DOCUMENTS 107441   6/1939   Australia.

OTHER PUBLICATIONS

American Orthodontics, "Maximum Retention Bands," advertisement placed in the Journal of Clinical Orthodontics, vol. XXVIII, No. 9, Sep. 1994.

Primary Examiner—Cary E. O'Connor
Attorney, Agent, or Firm—Christie, Parker & Hale, LLP

[57] ABSTRACT

An adjustable band for orthodontic use which is formed of a strip of relatively soft material, such as annealed metal or flexible plastic, is provided. In one embodiment, one end of the band contains tabs which are formed into a shackle and flexible projections. The other end of the band comprises a tang which contains rectangular indentations into which the projections fit. In another embodiment of the invention, the band is formed in a one-piece construction of molded plastic. The band of the second embodiment comprises a strip having a tang portion on one end and a shackle portion on its opposite end, where the shackle incorporates a slot through which the tang can be inserted. In both embodiments, when the tang is placed into the shackle, a cylindrical loop is formed which can be placed over a tooth and drawn into approximately the diameter of the tooth. Further tightening creates forces which shape the band around the tooth to match the contour of the tooth.

16 Claims, 6 Drawing Sheets

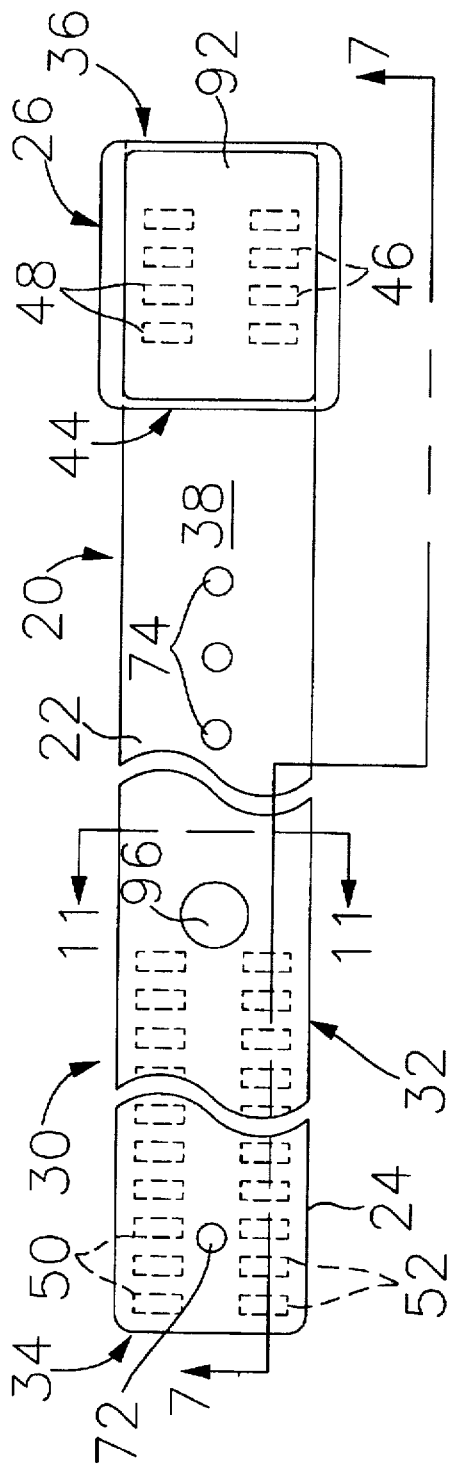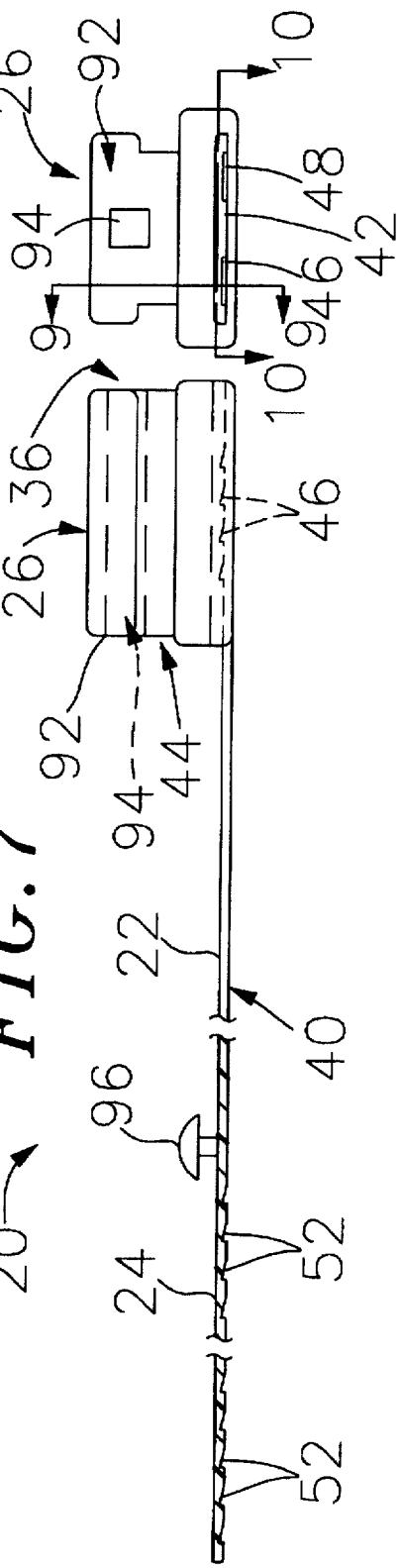

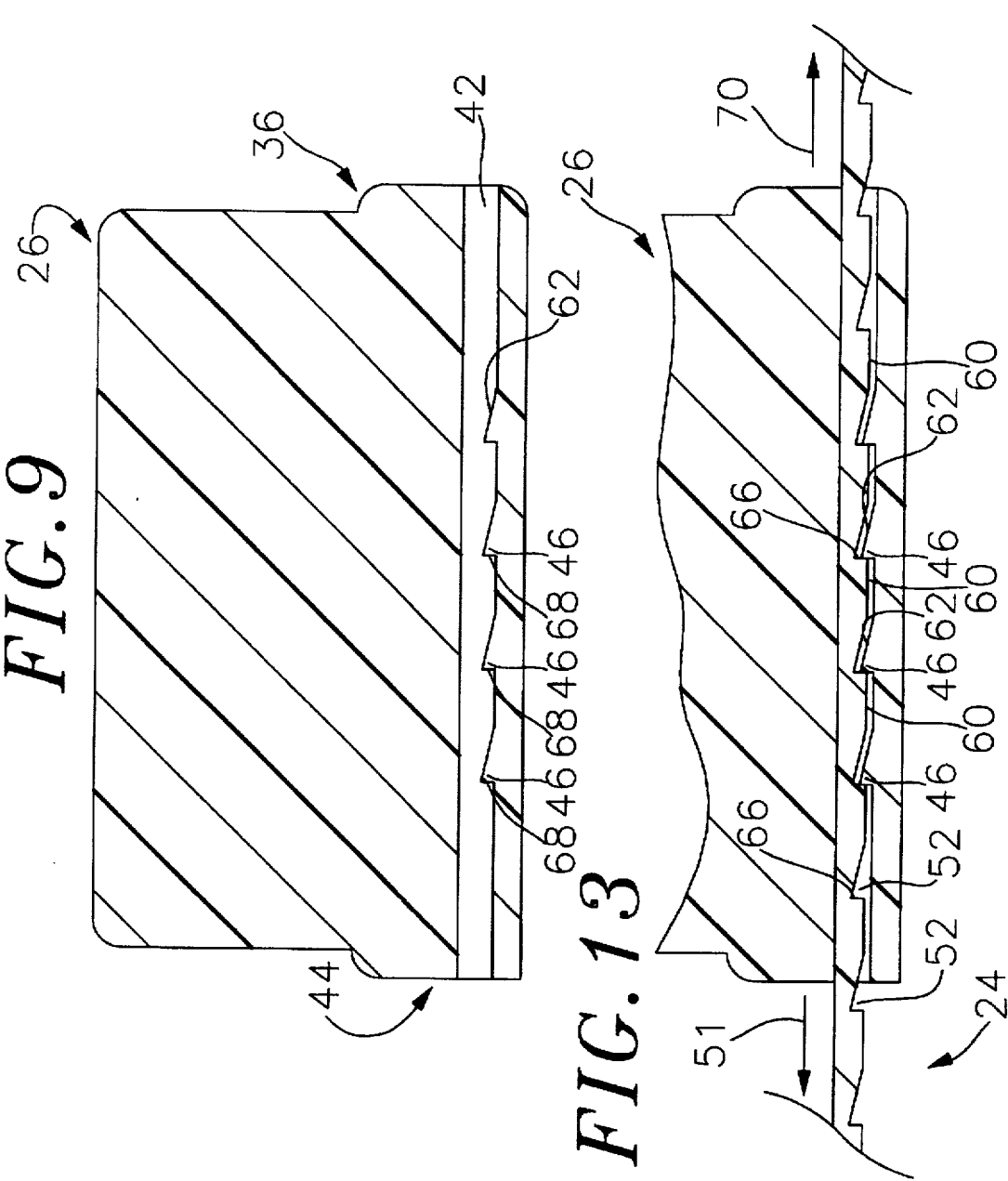

ORTHODONTIC BAND

CROSS-REFERENCE TO RELATED APPLICATION

This application is a continuation-in-part of application Ser. No. 08/326,065, filed Oct. 18, 1994, now abandoned, which is a continuation of Ser. No. 08/131,309, filed Oct. 4, 1993, now abandoned. Applications Ser. Nos. 08/326,065 and 08/131,309 are incorporated herein in their entirety by this reference.

FIELD OF THE INVENTION

The present invention relates to bands which are used to correct misplaced or misplaced teeth in orthodontic practice.

BACKGROUND OF THE INVENTION

Orthodontic bands have been used in the past in dentistry to serve as anchoring means for archwires and other dental appliances. The primary purpose of the bands is to exert pressure through the connecting wires on misplaced or misspaced teeth to cause the teeth to move to a desirable or proper position.

Originally, each band was individually fabricated and made to match the contour of the particular teeth for which it was intended. This required much hand work because of the barrel-like or ovate shape of the various teeth. Presently, many orthodontists use pre-formed bands but must stock a large number of sizes from which to select because of the various tooth sizes on which the bands are installed. Further, such pre-formed bands must still be altered to fit the contour of the particular tooth onto which it is applied.

The search for adjustable orthodontic bands has continued for more than 130 years. The objective has been to perfect a design which can be used for any tooth, is easily applied, and is relatively inexpensive to manufacture. Boyd et al (U.S. Pat. No. 2,007,517) and Lazarus (U.S. Pat. No. 3,138,872), among others, describe improved adjustable bands, but these still require a considerable amount of fitting. Burrell and Wilson (U.S. Pat. No. 4,840,562) teach an adjustable band which conforms to the shape of each tooth but requires a complex rack and pinion assembly for band installation.

There is still a need in the art for a band which readily conforms to the contour of a tooth, has a closing mechanism which is easy to manufacture and requires minimum adjustment by the orthodontist, and which is adaptable to a wide range of tooth sizes so that only a few lengths and widths need be stocked by the orthodontist.

Orthodontic bands can also incorporate a number of components, such as archwire brackets, buttons, hooks, tubes, and pins and the like, depending on the design of the particular band. In the past, such components have been attached to the band after the band was initially manufactured. Adding components to the band after its manufacture is time consuming and hence expensive.

There is a need in the art for a band which can be produced of one-piece construction already incorporating the desired attachments, such as hooks, tubes, covers, cleats, lugs, etc.

SUMMARY OF THE INVENTION

In one embodiment of the present invention, an elongated dental appliance is provided which is adapted to be fitted as an adjustable annular band encircling a tooth. The adjustable band comprises a shackle at one end and a tang at the other end. The shackle contains two vertically separated, evenly spaced rows of flexibly mounted, inclined, rectangular projections. The tang incorporates two vertically separated rows of rectangular indentations, wherein, when the tang is inserted into the shackle and the loop is closed, the projections are able to move horizontally from indentation to indentation in one direction but will resist forces in the reverse direction which could cause opening of the band.

In another embodiment of the present invention, an elongated dental appliance is provided which is formed in a one-piece construction of molded plastic. The appliance comprises a flexible plastic strip having a tang portion on one end and a shackle portion on its opposite end. The shackle has a slot through which the tang is inserted to form the band. Latching means are on the tang and in the shackle slot for latching the tang in the shackle slot while preventing withdrawal of the tang from the slot. A bracket which is molded integrally with the shackle incorporates a slot for accommodating an archwire.

BRIEF DESCRIPTION OF THE DRAWINGS

These and other features, aspects, and advantages of the present invention will be more fully understood when considered with respect to the following detailed description, appended claims, and accompanying drawings, wherein:

FIG. 6 is a semi-schematic, fragmentary, front plan view of another embodiment of a dental appliance provided in accordance with practice of the present invention comprising a plastic strip having a tang portion on one end and a shackle portion on its opposite end adapted to be fitted as an annular orthodontic band encircling a tooth;

FIG. 7 is a side plan view of the orthodontic band of FIG. 6;

FIG. 8 is an end view of the orthodontic band of FIG. 6, showing the shackle assembly;

FIG. 9 is a cross-sectional view taken along line 9—9 of FIG. 8;

FIG. 13 is a cross-sectional view of the shackle arrangement showing the interlocking of the grooves of the tang with the teeth of the shackle.

DETAILED DESCRIPTION

Figure 1:
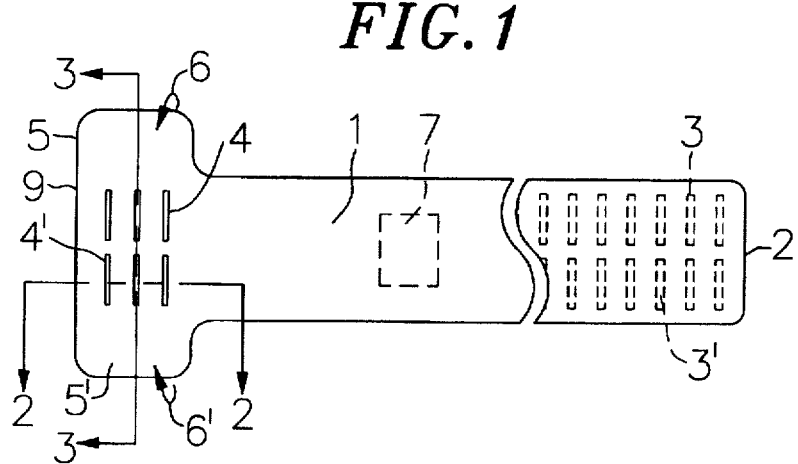
FIG. 1 is a plan view of one embodiment of a dental appliance adapted to be fitted as an adjustable orthodontic band provided in accordance with practice of principals of the present invention which includes an attached bracket.
Figure 2:
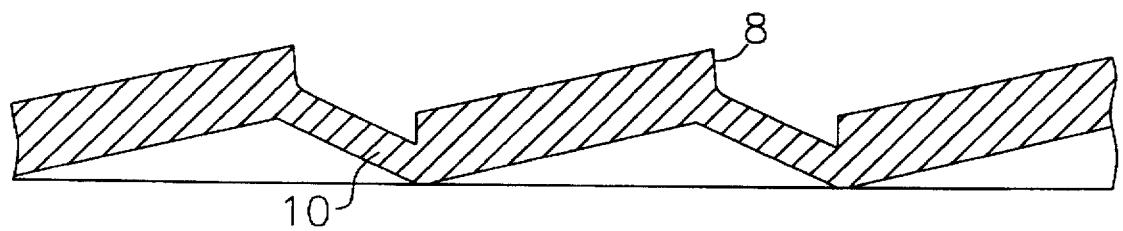
FIG. 2 is a cross-section view taken along line 2—2 of FIG. 1.
Figure 3:
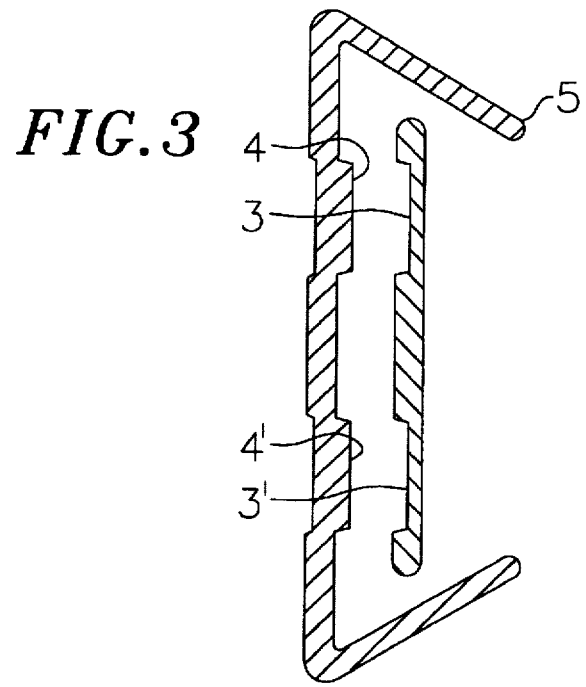
FIG. 3 is cross-section of a partially assembled band with its tabs partly closed as taken along line 3—3 of FIG. 1.

Referring to FIGS. 1-5, a first preferred embodiment of the orthodontic band of the present invention can be understood. Turning particularly to FIG. 1, there is shown a top view of a fabricated band blank with the addition of a bracket. The band 1 includes a tang end 2 and a shackle end 9 which embody the tabs 5 and 5' which may be folded over in directions 6 and 6' (FIGS. 1 and 3) to form a shackle. The entire band is formed in an approximately cylindrical form by inserting the tang end of the band into the shackle. Band material can be an annealed stainless steel, a precious metal alloy which has been softened by heat treatment, or any other corrosion resistant sheet material which displays a "dead soft" behavior. The band can also be made of certain types of plastic, for example, various grades of polycarbonate, nylon, polyurethane, or the like.

Figure 4:
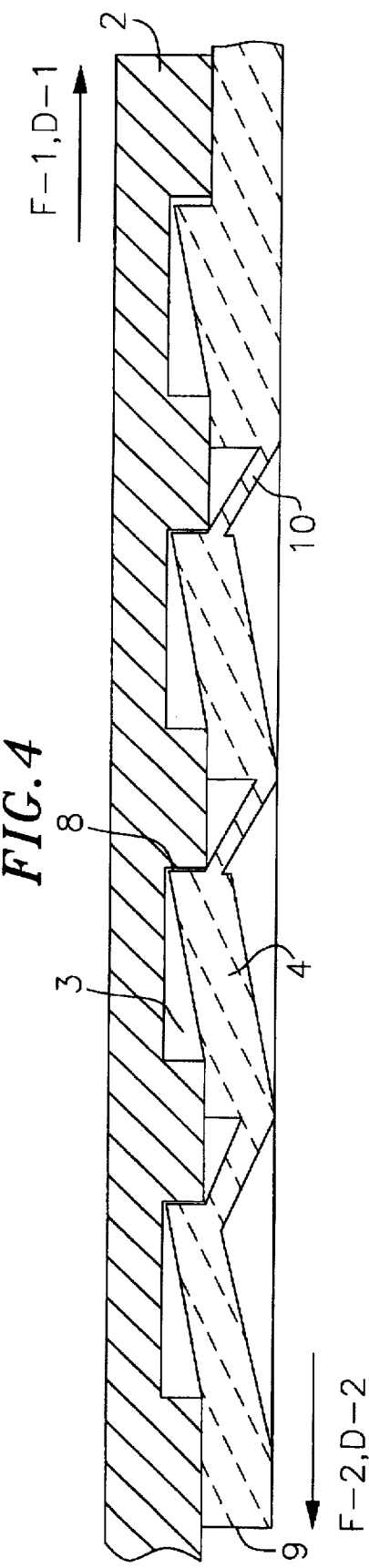
FIG. 4 is a schematic cross-sectional view of the embodiment of the orthodontic band shown in FIG. 1 illustrating the one-way action of raised and indented portions of the band when these surfaces are forced to move along one another.

The tang end is prepared by forming a series of rectangular indentations 3 in the upper half and indentations 3' in the lower half. Typical dimensions of these indentations are 1.00 mm long by 0.4 mm wide by 0.1 mm deep, with the bands being 3.5 mm wide, 0.13 mm thick, and from 35 mm to 45 mm long. The inside of the shackle is initially prepared with three upper and three lower sets of projections 4 and 4' having the special shape shown in FIG. 2. The metal thickness is reduced at 10 to impart flexibility to each adjoining projection. A sharp cornered rectangular projection is formed at 8. When the tang 2 is inserted into the shackle, the rectangular indentations 3 and 3' come into contact with the specially shaped projections 4 and 4', as shown in FIG. 4. As the band loop so formed is drawn up by forcing the tang further into the shackle and past it (direction D-1 and force F-1, FIG. 4), the edges 8 of the projections ride up on the edges of the rectangular indentations 3 and 3'. If the direction is reversed, however, the edges 8 drop back and come to rest against the corners 10 of the tang's indentations. The band's closure is thus made irreversible. The band's one-way operation is similar to that produced by a pawl and ratchet. The indentations and projections can be formed in the band material by coining or electrospark machining, or the like.

Figure 5:
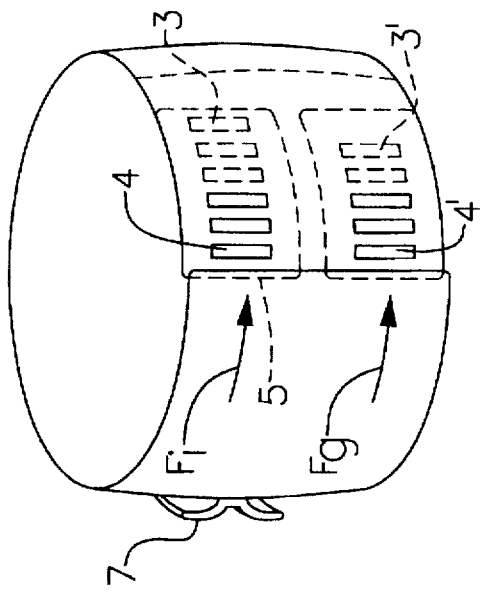
FIG. 5 is a schematic perspective view of an assembled and partially shaped band ready for final shaping onto a particular tooth.

Because of the double row of indentations in the tang and the double row of projections in the shackle, it is possible to achieve separate torques in the incisal and gingival portions of the band and thus produce conformance to tooth contour by forces applied at $F_i$ and $F_g$ (FIG. 5).

Because the tabs 5 and 5' are against the surface of the tooth, tightening of the band forces the tabs to hold the band with more and more pressure as tightening progresses.

The present invention needs to be stocked in relatively few lengths and widths to cover a large number of tooth sizes.

In the flat form, these bands are easily worked on to add brackets, hooks, tubes, and other orthodontic fixtures. For example, an archwire bracket 7 is shown mounted on the band 1 in FIGS. 1 and 5. This reduces working time and makes the orthodontic process less time consuming.

A second embodiment of the present invention can be understood by referring to FIGS. 6-14. Referring particularly to FIGS. 6 and 7, there is shown an elongated dental appliance 20 which is adapted to be fitted as an annular band encircling the patient's tooth. The dental appliance is formed in a one-piece construction by conventional injection molding of a plastic or reinforced plastic material such as polycarbonate, nylon, various grades of polyurethane, or the like. Such reinforcing can be made by the use of fiberglass, carbon fibers, and various mineral fillers as are well known in the art.

The appliance 20 comprises a flexible plastic strip 22 which includes a tang portion 24 on one end and shackle portion 26 on its opposite end. The components of the dental appliance will be described below in relation to one another as the appliance is shown in FIGS. 6 and 7 with a top 30, a bottom 32, a left end 34, and a right end 36, where the outer surface 38 of the band is the surface which faces away from the patient's tooth, and the inner surface 40 of the band (shown only in FIG. 7) is the surface which contacts the patient's tooth when the device is in place on the tooth.

Figure 10:
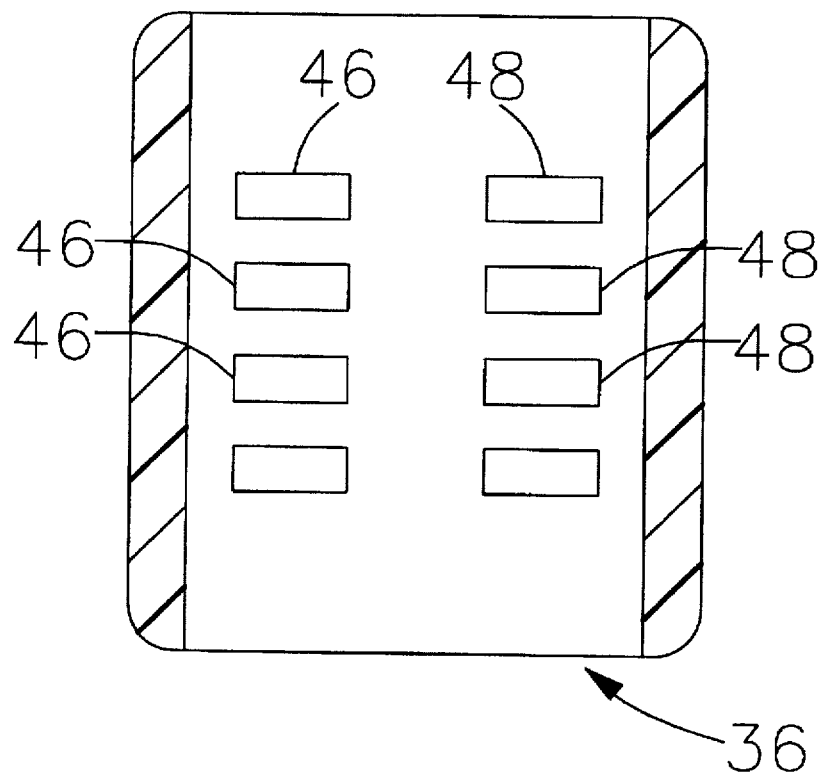
FIG. 10 is a cross-sectional view taken along line 10—10 of FIG. 8.

Turning to FIGS. 8 and 9 in addition to FIGS. 6 and 7, the shackle portion 26 of the device or band is formed with an elongated slot 42 which extends through a lower portion of the shackle from its right side end 36 through its left side end 44. Turning to FIG. 10 in addition to FIGS. 8 and 9, the slot 42 incorporates two vertically spaced-apart rows of teeth 46 and 48, respectively, with only one of the rows 46 seen in the FIG. 9 cross-section.

As is seen in FIGS. 6 and 7, the tang portion 24 of the strip 22 incorporates two vertically spaced-apart rows of indentations 50 and 52 which, as is described below in greater detail, engage the teeth 46 and 48 in the slot of the shackle when the band is being tightened around a patient's tooth.

In one exemplary embodiment of the present invention, the tang end of the strip 22 is 3.2 mm wide, 0.15 mm thick, and is 49 mm in length. The slot 42 in the shackle is approximately 3.25 mm wide and is 0.25 mm high.

Figure 14:
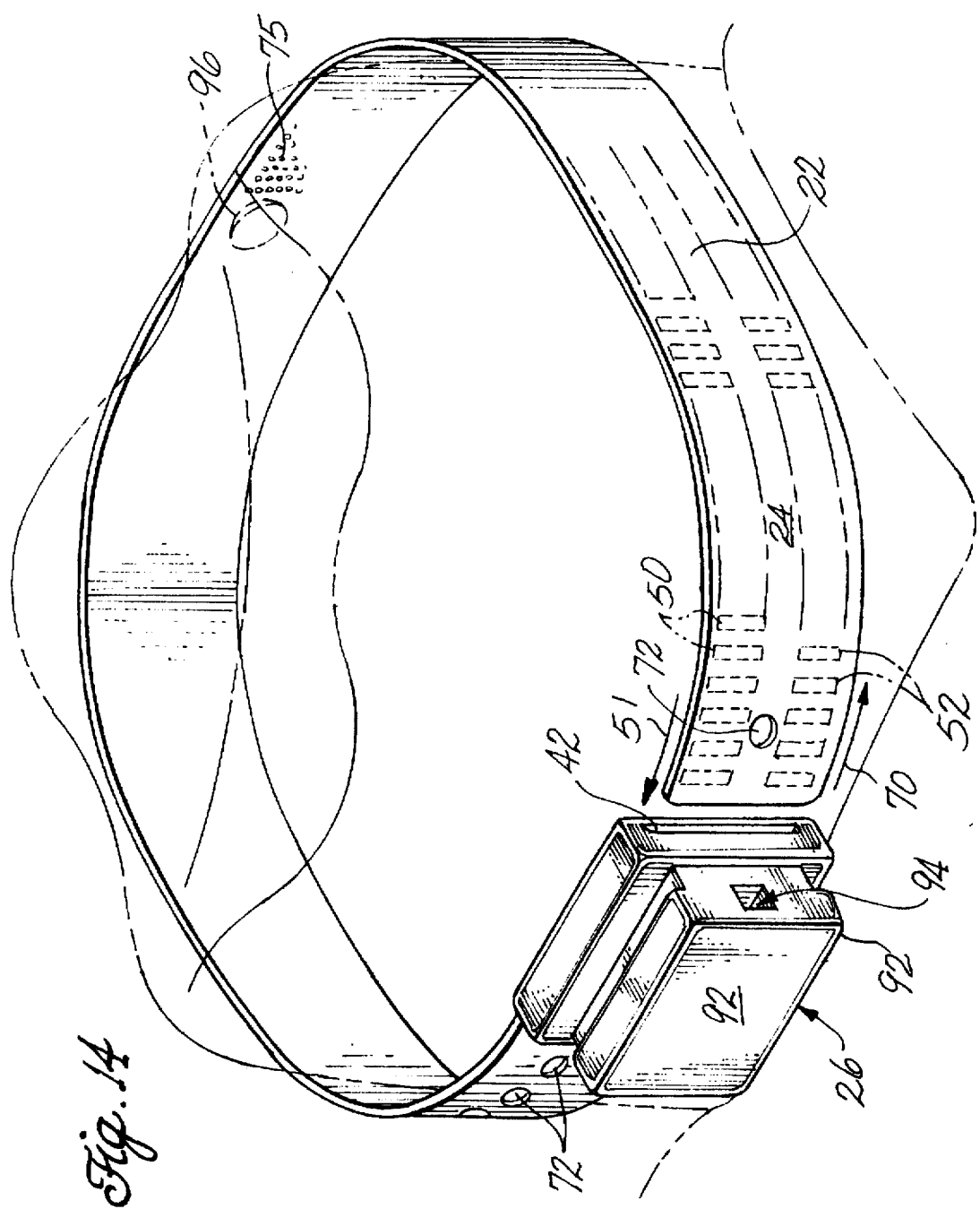
FIG. 14 is a semi-schematic perspective view of the dental appliance shown in FIG. 6, with the tang end in place ready for insertion into the shackle end to thereby form the band.

Turning to FIG. 13, which is a cross-section showing the tang 24 in the shackle slot 42, and FIG. 14, which shows the device being formed as a band with the tang 24 ready for insertion into the shackle slot 42, the process of tightening of the band around the patient's tooth (shown in phantom in FIG. 14) can be understood. The tang end 24 of the band is inserted into the shackle slot 42 and the band is tightened by moving the tang in the direction of the arrow 51 shown in FIGS. 13 and 14. As the band loop being formed is drawn up by forcing the tang further into and through the shackle slot 42 (in the direction of the arrow 51), the flats 60 on the tang slide up the tooth ramps 62 from tooth to tooth. The teeth 46 are designed to mate with the corresponding indentations in the tang so that the tang can move in only one direction in the slot; namely, in the direction shown by the arrow 51 which tightens the band. Thus, the tang 24 can be moved in the direction of the arrow 51 until the band is desirably tight, but it cannot be moved in the opposite direction. If the direction is reversed, i.e., if an attempt is made to move the tang in a band-loosening direction, the vertical edges 66 which define the leading edge of the tang indentations will butt up against the vertical leading edges 68 of the teeth. The engagement of the edges 66 of the tang indentations with the leading edges 68 of the teeth inhibit the tang 24 from moving in the direction of the arrow 70 (FIGS. 13 and 14), i.e., in the direction which would loosen the band. The provision of the design which accommodates movement of the tang in only one direction in the shackle slot, i.e., the tightening direction, ensures that once the band is tightened in place on the tooth, it cannot come loose. However, further tightening of the band at some later time to accommodate stretching of the band material or the like is possible by simply moving the tang further in the direction 51. While a particular configuration of teeth and indentations is illustrated, it should be understood that other designs can also be used so long as the result is a one-way operation as is the case with the shackle teeth 46, 48 and the tang indentations 50, 52. Also, if desired, the teeth can be on the tang and the indentations can be in the shackle slot.

In the illustrated embodiment, because the teeth 46 and 48 are in the shackle slot, there are no sharp projections associated with the latching components or any other portions of the band which bear against the tooth surfaces when the band is on the tooth. Thus, the band surface which contacts the tooth does not incorporate any component that will abrade or otherwise irritate the tooth surface.

In one embodiment of practice of the present invention (shown in FIGS. 6 and 14), a hole or perforation 72 is in the outer surface of the tang end, and a row of horizontally spaced-apart indentations 74 are in the outer surface of the strip 22 adjacent the shackle 26. The perforation 72 and indentations 74 are adapted for engagement of a tool which is used to exert leverage to pull the tang through the slot to thereby tighten the band.

In a preferred embodiment of practice of the present invention, the surface of the band which contacts the patients tooth has a smooth texture 75 (best seen in FIG. 14) to enhance the engagement between the band and the tooth. If desired, a dental adhesive such as a zinc phosphate cement, a polycarboxylate cement, or a glass ionomer, as are well known in the art, can be used to fix the band to the tooth. The textured inner band surface enhances the bond between the tooth and band, but the texturing does not provide a sharp surface which could abrade the tooth.

Figure 11:
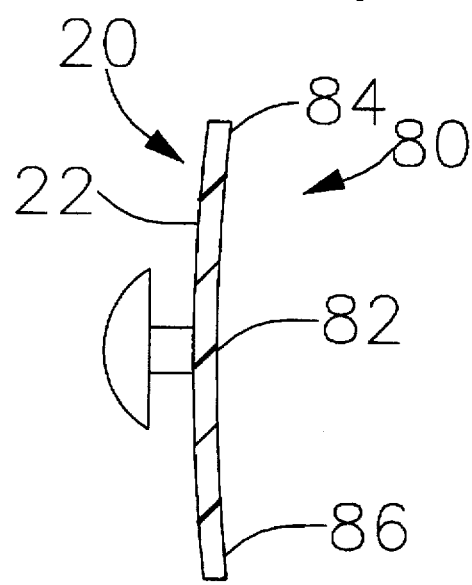
FIG. 11 is a cross-sectional view taken along line 11—11 of FIG. 6, showing the curved shape of the strip portion of the dental appliance.

Turning to FIG. 11, there is shown a cross-section of the strip 22 having a curvature 80 in the same direction as a tooth, i.e., the concave surface 82 contacts the tooth, so that when the band is pulled tightly around a tooth, the top and bottom portions 84 and 86, respectively, of the band fit snugly against the tooth. This tight fit is desired so that no pockets or loose areas are created in which food can become lodged.

Figure 12:
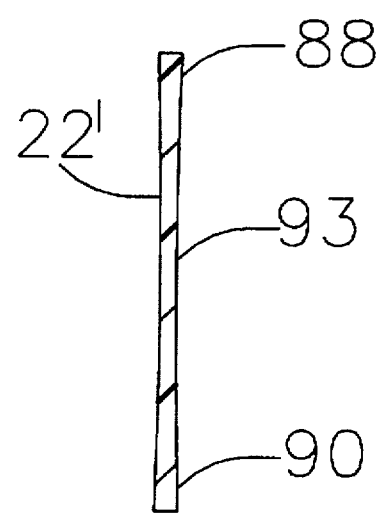
FIG. 12 is a cross-sectional view showing the shape of another embodiment of the strip portion of the dental appliance.

Turning to FIG. 12, there is shown another embodiment of a strip 22' provided in accordance with practice of the invention where the strip is thicker at its top 88 and bottom 90 and is thinner in its center 93. Having a band of the configuration of FIG. 12 provides for increased stretch of the plastic material in its center to thereby better form to the shape of the tooth while being able to be pulled tightly against the tooth at its top and bottom. In an exemplary embodiment, the strip 22' is 1.5 mm thick at its top and bottom and 1.0 mm thick in its center. Because the plastic material of the band can stretch, it is also possible to tighten one or the other of the top or bottom portions of the band more tightly than the other portion. For example, the top portion of the band can be tightened more than the bottom portion by moving the upper shackle tooth/tang indentation combination (48, 50) one or more notches farther in the tightening direction than the lower shackle tooth/tang indentation combination (46, 52). Conversely, the bottom of the band can be made tighter than the top by moving the lower shackle tooth/tang indentation combination (46, 52) one or more notches farther than the upper shackle tooth/tang indentation combination.

Turning again to FIGS. 6, 7, 8, and 14, a bracket 92 is molded integrally with the shackle and incorporates a slot 94 for accommodating an archwire. In the embodiment shown, the slot is covered. In an alternative embodiment, the slot can be molded in an open condition or can be molded such that it is initially covered, with the cover incorporating a series of perforations along the slot so that the cover can be removed, thereby uncovering the slot. Because the bracket 92 is made of a plastic material, it has what is called an "elastic memory." For example, when plastic is changed in shape due to the application of a force, it exerts a force in the opposite direction, tending to reform (spring back) to its original B0 shape. This elastic memory provides an advantage to the band of the present invention over bands that are made out of less elastic material such as metal or the like. For example, when an archwire is inserted into the slot 94 of the bracket 92 and force is applied to the archwire, it tends to move a portion of the bracket on which the archwire bears in the direction of the force. The bracket then exerts a force on the archwire as it tends to come back to its original shape, which aids in moving the tooth to the desired position.

Referring to particularly to FIGS. 6 and 7, the band 20 includes a button 96 which is a typical button provided on such orthodontic bands. In practice of the present invention, both the button and the bracket, and other attachments required for such orthodontic bands, such as hooks, tubes, covers, cleats, lugs or the like, are provided in one integral plastic molding step and provide a band of one-piece construction. Conversely, prior art bands which, for example, are made of metal, require that such buttons, brackets, and other attachments, be welded or otherwise attached to the band blank after the band blank has been formed. The extra fabrication steps required to affix the various attachments to prior art bands makes the manufacture of prior art bands more expensive than the single molding process which provides the one-piece band of the present invention.

The above descriptions of exemplary embodiments of an adjustable band for use in orthodontic dentistry are for illustrative purposes. Because of variations which will be apparent to those skilled in the art, the present invention is not intended to be limited to the particular embodiments described above. The scope of the invention is described in the following claims.

What is claimed is:

1. An adjustable orthodontic band having first and second ends and being configured to be formed in a closed loop around a tooth, the band comprising;

a shackle on the first end of said band having two vertically separated, evenly spaced rows of flexibly mounted, inclined projections thereon; and a tang on the second end of said band having two vertically separated rows of rectangular indentations thereon, said indentations on said tang configured to mate with a corresponding one of said projections on said shackle when said tang is inserted into the shackle and the loop is closed;

wherein the projections are able to move from indentation to indentation as the loop is being closed, but when forces are applied in the reverse direction to open the loop, the projections engage the rectangular indentations, thereby inhibiting the band from being opened.

2. An adjustable band an claimed in claim 1, wherein the vertical separation of the two rows of projections and indentations results in the production of forming forces in the incisal and gingival planes of any tooth around which the band is installed to shape the band in accordance with the contour of said tooth.

3. An adjustable band as described in claim 2, wherein said shackle comprises tabs, and wherein the tab ends of said shackle are in contact with the surface of said tooth, resulting in the tightening of the shackle tabs as the loop is closed.

4. An elongated dental appliance which is adapted to be fitted as an annular band encircling a tooth, the dental appliance formed in a one-piece construction of molded plastic, said appliance comprising:

a flexible plastic strip having a tang portion on one end and a shackle portion on its opposite end, said shackle incorporating a slot through which the tang is inserted to form the band;

an upper row and a lower row of vertically spaced apart indentations in the tang which are engaged by corresponding upper and lower rows of vertically spaced apart teeth in the shackle slot for latching the tang in the shackle slot while preventing withdrawl of the tang from the slot, said flexible strip formed of a plastic that can stretch sufficiently so that one or the other of the upper or lower portions of the band can be tightened more than the other portion by moving the upper or lower shackle tooth/tang indentation combination one or more notches farther in the tightening direction than the other shackle tooth/tang indentation combination; and a bracket molded integrally with the shackle having a slot for accomodating an archwire.

5. The dental appliance of claim 4, wherein the flexible plastic strip is thicker along its edges and thinner in its center.

6. The dental appliance of claim 4, wherein the flexible plastic strip is curved.

7. The dental appliance of claim 4, wherein the flexible plastic strip has a perforation in its outer surface at the tang end and a plurality of indentations in its outer surface adjacent the shackle, said indentations adapted for engagement of a tool for pulling the tang end through the slot to thereby tighten the band.

8. The dental appliance of claim 4, wherein the archwire slot is open.

9. The dental appliance of claim 4, wherein the archwire slot is covered.

10. The dental appliance of claim 4, wherein said band is configured so that when it is mounted on the tooth, the band surface which contacts the tooth is absent any sharp projections.

11. The dental appliance of claim 4, wherein the flexible plastic strip has a smooth texture on that portion of the surface which contacts the tooth.

12. The dental appliance of claim 4, wherein the archwire slot is covered by a removable cover.

13. An elongated dental appliance which is adapted to be fitted as an annular band encircling a tooth, where an upper portion of the band is around an upper portion of the tooth and a lower portion of the band is around a lower portion of the tooth, the dental appliance formed in a one-piece construction of molded plastic, said appliance comprising:

a flexible plastic strip having a tang portion on one end and a shackle portion on its opposite end, the shackle incorporating a slot through which the tang is inserted to form the band, said plastic strip being thicker along its edges and thinner in its center;

an upper row and a lower row of vertically spaced apart indentations in the tang which are engaged by corresponding upper and lower rows of vertically spaced apart teeth in the shackle slot to thereby latch the tang in the shackle slot while preventing withdrawal of the tang from the slot, said flexible strip being formed of a plastic that can stretch sufficiently so that one or the other of the upper or lower portions of the band can be tightened more than the other by moving the upper or lower shackle tooth/tang indentation combination one or more notches farther in the tightening direction than the other shackle tooth/tang indentation combination; and a bracket molded integrally with the shackle, said bracket having a slot for accommodating an archwire, wherein said archwire slot is removably covered.

14. The dental appliance of claim 13, wherein the flexible plastic strip is curved.

15. The dental appliance of claim 13, wherein the flexible plastic strip has a perforation in its outer surface at the tang end and a plurality of indentations in its outer surface adjacent the shackle, said indentations adapted for engagement of a tool for pulling the tang end through the slot to thereby tighten the band.

16. The dental appliance of claim 13, wherein the flexible plastic strip has a smooth texture on that portion of the surface which contacts the tooth.

\* \* \* \* \*

UNITED STATES PATENT AND TRADEMARK OFFICE
CERTIFICATE OF CORRECTION

PATENT NO. : 5,697,783
DATED : December 16, 1997
INVENTOR(S) : Mark J. Wilson; Frank J. Burrell, Jr.; Farel A. Rosenberg It is certified that error appears in the above-indentified patent and that said Letters Patent is hereby corrected as shown below:

On the title page,
Item 56, Refeferences Cited, U.S. Patent Documents,
      Replace "1,304,881  3/1919  Johnson"
      with -- 1,304,881  5/1919  Johnson --.
Column 1, line 15, change "misplaced" to -- misspaced --. (second occurrence)
Column 2, line 30, change "cross-section" to -- cross-sectional --.
Column 2, line 32, replace "is cross-section" with -- is a cross section --.
Column 5, line 16, change "patients" to -- patient's --.
Column 5, line 67, after "original" delete "B0".
Column 6, line 9, after "Referring" delete "to".

Signed and Sealed this

Fifteenth Day of September, 1998

Attest:

BRUCE LEHMAN

*Attesting Officer*      *Commissioner of Patents and Trademarks*